United States Patent [19]
Lecuyer

[11] Patent Number: 5,368,556
[45] Date of Patent: Nov. 29, 1994

[54] IMPLANTABLE DRAINAGE VALVE FOR THE TREATMENT OF HYDROCEPHALUS

[75] Inventor: Alain Lecuyer, Grasse, France

[73] Assignee: Cordis Corporation, Miami Lakes, Fla.

[21] Appl. No.: 207,890

[22] Filed: Mar. 7, 1994

Related U.S. Application Data

[63] Continuation of Ser. No. 7,066, Jan. 21, 1993, abandoned.

[30] Foreign Application Priority Data

Jan. 22, 1992 [FR] France ................... 92 00671

[51] Int. Cl.⁵ ............................................. A61M 5/00
[52] U.S. Cl. ............................................. 604/8; 604/9;
604/247; 604/249; 137/38; 137/529; 137/539
[58] Field of Search ............................ 137/38–39,
137/529, 539; 128/DIG. 25; 600/29–31;
604/246, 247, 249, 256, 335, 8–9

[56] References Cited

U.S. PATENT DOCUMENTS

| | | |
|---|---|---|
| 3,288,142 | 11/1966 | Hakim ................... 604/247 |
| 3,683,929 | 8/1972 | Holter ................... 604/247 |
| 3,886,948 | 6/1975 | Hakim . |
| 3,889,687 | 6/1975 | Harris et al. . |
| 3,924,635 | 12/1975 | Hakim . |
| 4,106,510 | 8/1978 | Hakim et al. . |
| 4,332,255 | 6/1982 | Hakim et al. . |
| 4,387,715 | 6/1983 | Hakim et al. . |
| 4,540,400 | 9/1985 | Hooven . |
| 4,551,128 | 11/1985 | Hakim et al. . |
| 4,557,721 | 12/1985 | Hooven . |
| 4,595,390 | 6/1986 | Hakim et al. . |
| 4,627,832 | 12/1986 | Hooven et al. . |
| 4,675,003 | 6/1987 | Hooven ................... 137/539 |
| 4,676,772 | 6/1987 | Hooven . |
| 4,681,559 | 7/1987 | Hooven . |
| 4,705,499 | 11/1987 | Hooven . |
| 4,714,458 | 12/1987 | Hooven . |
| 4,714,459 | 12/1987 | Hooven . |
| 4,729,762 | 3/1988 | Doumenis . |
| 4,769,002 | 9/1988 | Hooven . |
| 4,776,838 | 10/1988 | Sainte-Rose et al. . |
| 4,776,839 | 10/1988 | Doumenis . |
| 4,781,672 | 11/1988 | Hooven . |
| 5,042,974 | 8/1991 | Agarwaz ................... 604/247 |

*Primary Examiner*—David Isabella
*Assistant Examiner*—P. Zuttarelli
*Attorney, Agent, or Firm*—Lockwood, Alex, Fitzgibbon & Cummings

[57] ABSTRACT

An implantable drainage valve for the treatment of hydrocephalus is described. The valve includes a body, a valve seat, a closure member, a spring and at least one spherical weight. The spring is positioned within the cylindrical chamber of the valve body and between the closure member and the spherical weight. The valve is intended to be vertically oriented when the patient is sitting or standing and, when so oriented, the weight will provide additional compressive force against the spring to help maintain the valve in a closed condition. Consequently, hyperdrainage is avoided when the valve experiences normal variations in fluid pressure differentials such as when the patient rises from a lying or recumbent position to a standing position.

17 Claims, 1 Drawing Sheet

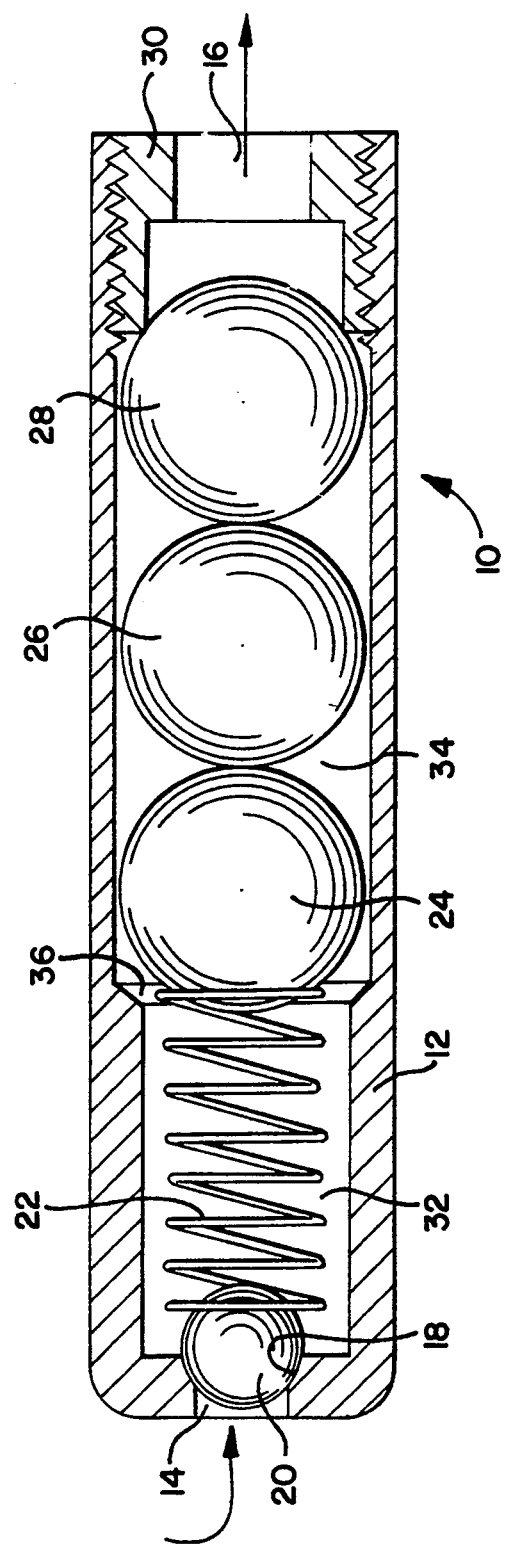

IMPLANTABLE DRAINAGE VALVE FOR THE TREATMENT OF HYDROCEPHALUS

This application is a continuation of application Ser. No. 08/007,066, filed Jan. 21, 1993, now abandoned.

BACKGROUND AND BRIEF DESCRIPTION OF THE INVENTION

This invention relates to medical devices and specifically to devices which are effective in the treatment of hydrocephalus. More specifically, the invention relates to an implantable drainage valve for draining excess cerebrospinal fluid ("CSF") from the brain to a drainage area elsewhere in the body.

Hydrocephalus is a condition in which the body, for any of several reasons, is unable to relieve itself of excess CSF collected in the ventricles of the brain, resulting in increased epidural and intradural pressures. This in turn causes adverse physiological effects including compression of brain tissue, impairment of blood flow in the brain tissue and impairment of the brain's normal metabolism.

Various types of drainage valves have been used in the treatment of hydrocephalus. Generally, these valves allow for the controlled drainage of excess CSF from the brain to a suitable drainage area in the body such as the peritoneal cavity, for example. CSF drainage valves include check valves, servo valves and combinations thereof. Check valves operate by opening when the fluid pressure differential between their inlet and outlet openings exceeds a certain predetermined threshold value.

Noted drawbacks in the use of simple check valves include their failure to compensate for the differences in liquid column height which result when the patient stands after lying in a recumbent position. In these situations, the differential fluid pressure normally increases by reason of the resulting increased vertical height of the fluid column existing between the head and the selected drainage location. Though such an increase in differential pressure is normal, a simple check valve will typically respond by opening and thereby allowing undesired hyperdrainage of the ventricular spaces which may result, for example, in a potentially serious hematoma. Accordingly, it is desirable to provide a hydrocephalus pressure relief valve which is effective in shunting CSF in response to abnormal intracranial pressures while avoiding hyperdrainage in the event of normal variations in fluid pressures.

One solution proposed to mitigate such drawbacks in simple check valves has been to add an additional valve body in series with the original check valve. In this arrangement, a check valve is combined in series with an additional valving mechanism intended to prevent the valve from opening in response to normal CSF pressure variations. The typical check valve includes a ball valve held in a tapered valve seat under the force of a compression spring. When CSF pressure exceeds a predetermined threshold, the fluid pressure unseats the ball to allow fluid to pass through the valve. A second valve body is provided in series with the check valve to prevent CSF drainage in those situations where the check valve has opened in response to normal fluid pressure differentials.

One example of such a second valve body includes a second tapered end seat with a second ball valve seated therein to control the flow of fluid from the check valve through the second body. Spherical weights are positioned within the second valve body to hold the second ball valve in its valve seat under the influence of gravity when the device is vertical. In this arrangement, the additional spherical weights maintain the valve in a closed condition in those instances where the check valve might open in response to the normal pressure differentials experienced by the valve, such as when the patient rises to a standing position. These valves, however, are expensive, requiring the accurate machining of at least two tapered valve seats, and, the inclusion of additional valve parts have made such valves rather bulky, requiring lumbar implantation. Finally, combined valves of this type may experience undesirable dynamic or ballistic effects when the patient engages in jerking movements such as running or jumping. These dynamic effects may adversely interfere with the proper operation of the valve.

The present invention overcomes the problems of the prior art and meets the aforementioned goals by providing a pressure relief valve which prevents excessive drainage of CSF in the event of normal increases in differential pressure and which is inexpensive to manufacture and is designed for cranial implantation. In the preferred embodiment, the valve is provided in a cylindrical housing including a single ball valve seated in a tapered valve seat and retained therein under the force of a compression spring. At least one spherical weight is positioned in the housing to coact with the ball valve and compression spring to keep the valve in a closed condition when the valve experiences normal variations in CSF pressure.

Possible ballistic or dynamic effects are further minimized in the valve design of the present invention due to the direct mechanical relationship between the closure member, the compression spring and the spherical weights housed within the cylindrical housing. An adjustment screw is provided in association with the housing and the spherical weights to set the valve to open at a predetermined fluid pressure.

It is accordingly an object of the present invention to provide a device for the relief of excess cerebrospinal fluid pressure and useful in the treatment of hydrocephalus and the like.

It is another object of the present invention to provide a drainage valve suitable for cranial implantation and useful in the treatment of hydrocephalus.

It is another object of the present invention to provide a drainage valve useful in the treatment of hydrocephalus and which prevents excessive drainage of CSF in the event of normal increases in differential fluid pressure such as when a patient stands after lying in a recumbent position.

These and other objects of the present invention will be more clearly understood upon consideration of the remainder of the disclosure, including the detailed description of the preferred embodiment and the appended claims.

BRIEF DESCRIPTION OF THE DRAWING

The FIGURE is an enlarged sectional view of a valve according to the invention and showing the interrelationship of the component parts thereof.

DETAILED DESCRIPTION OF THE PREFERRED EMBODIMENT

The present invention provides an implantable valve for the controlled drainage of CSF from a ventricle of the brain to a suitable drainage location of the body. A cylindrical valve body houses a spherical closure member or ball retained within a tapered valve seat by the force exerted by a compression spring. At least one spherical weight is provided within the housing to maintain the valve in a closed condition when the cylindrical valve experience normal variations in CSF pressure. Under the influence of gravity, the spherical weight provides additional compressive force against the compression spring to maintain the closure member within its valve seat. In describing the details of the preferred embodiment, reference is made to the drawing wherein the described elements are identified with reference numerals to fully illustrate the discussed structure.

Referring now to the drawing, a sectional view of the invention is shown, illustrating its inner mechanism. The valve 10 has a cylindrical body 12 having an upstream opening 14 at one end of the body 12 and a downstream opening 16 at the other end thereof. When the valve 10 is implanted in the cranium of a patient, the upstream opening 14 is in fluid communication with a ventricle of the brain, typically by means of a ventricular catheter (not shown) which is normally radio-opaque to facilitate accurate placement within the brain. The outlet port or downstream opening 16 of the valve 10 is typically attached to one end of a drain catheter (not shown), the opposite end of which discharges CSF into an appropriate location of the patients body such as the right atrium of the heart or the peritoneal cavity. When opened, the valve allows passage of CSF from the brain ventricles and through the hollow body 12, as indicated by the flow arrows in the drawing, to the selected discharge location to thereby relieve excessive CSF pressure.

A tapered valve seat 18 is provided at the innermost portion of the upstream opening 14 to seat therein a spherical closure member 20. When the closure member 20 is fully seated within the tapered valve seat 18, the flow of CSF fluid through the valve 10 is prevented. The valve is maintained in its closed condition by the force of a compression spring 22 pressing, at one end thereof, against the closure member 20 and holding it within the tapered valve seat when the CSF pressure differential across the valve 10 is below a first predetermined opening pressure. The other end of the spring 22 opposite the closure member 20 bears against a spherical weight 24.

It will be appreciated that the valve 10 is intended to be, when implanted, vertically oriented when the patient's head is upright, as in a sitting or standing position. Accordingly, the valve 10 will be substantially horizontal when the patient is in a recumbent position. The spherical weight 24 provides additional compressive force against the spring 22 whenever the valve is in a substantially vertical orientation. In this arrangement of parts, the weight 24 will exert additional force against spring 22 and the closure member 20 to assist in maintaining the valve 10 in a closed condition when the fluid pressure differential across the valve is below a second predetermined value in the event of sudden but normal increases in differential fluid pressure.

While a single weight 24 may be sufficient, the preferred embodiment includes additional spherical weights 26 and 28 which occupy the remaining interior of the body 12, providing additional force to compress the spring 22 against the closure member 20. An adjustment screw 30 bears against the spherical weight 28, snugly holding the weights 24, 26 and 28 between the screw 30 and the spring 22.

The interior of the valve body 12 is divided into an upstream section 32 and a downstream section 34 with the upstream section 32 being of a smaller internal diameter than the downstream section 34. Most preferably, the diameter of the upstream section 32 is smaller than the diameter of the weight 24, preventing the weight 24 from entering the upstream chamber and confining the three weights 24, 26 and 28 to the downstream section 34 within the body 12. A shoulder 36 is formed at the interface between the two internal portions 32 and 34 of the body 12 and serves to limit the travel of the weight 24.

When the valve is in its horizontal position, such as when the patient is lying down, the spherical closure member 20 is subjected only to the differential pressure between the upstream and downstream openings 14 and 16, respectively, and to the preset force exerted by the spring 22. When the patient rises, the valve 10 is reoriented to a vertical position with the downstream opening forming the uppermost portion of the valve 10. In this orientation, the spherical weights 24, 26 and 28 exert their combined weight under the influence of gravity against the spring 22. Accordingly, the closure member 20 experiences greater force in the vertical orientation from its downstream side, to hold the closure member 20 more securely within the tapered valve seat 18, thereby compensating for the change in height of the liquid column caused by the patient's rise to a standing or vertical position.

As seen in the FIG., the components of the valve of the present invention are contained within a single body 12 including a single tapered seat 18. Consequently, the valve is of a compact design which facilitates cranial implantation. Inclusion of a single valve seat helps to reduce manufacturing costs. Dynamic or ballistic effects experienced by some valves during jerking movements, such as when the patient is running or jumping, are minimized in the design of the present invention since the weights 24, 26 and 28 are held in place within the downstream portion 34 of the body 12 by the constant tension of the spring 22, pushing the weights against the innermost portion of the adjustment screws. Thus, even when the valve 10 is in a horizontal position, the weights 24, 26 and 28 are securely held between the spring 22 and the screw 30. Adjustments may be made to the minimum opening pressure of the valve 10 by adjustment of the screw 30 with a rotation of the screw resulting in an increased minimum opening pressure. The downstream opening 16 of the valve 10 extends through the center of the screw 30.

While a preferred embodiment of the invention has been described, it will be understood that various changes and modifications can be made to the described embodiment by those skilled in the art without departing from the true spirit and scope of the invention as defined in the following claims.

I claim:

1. A surgically implantable drainage valve for the treatment of hydrocephalus, comprising:
   a valve body;
   a valve seat within said valve body;
   a closure member dimensioned to be seated within said valve seat;
   a spring member within the valve body having a first end and a second end, said first end of said spring member securing said closure member in said valve seat; and a weight bearing against said second end of said spring member that provides additional force to compress the spring member against the closure member whenever the valve body is in a substantially vertical orientation.

2. The surgically implantable drainage valve of claim 1 wherein said valve body is cylindrical and said weight includes at least one spherical member housed within said valve body.

3. The surgically implantable drainage valve of claim 1 wherein said valve body is cylindrical having an upstream chamber and a downstream chamber therein, said upstream chamber, in cross section, having a diameter less than the diameter of said downstream chamber.

4. The surgically implantable drainage valve of claim 3 wherein said valve seat, said closure member and said spring member are positioned within said upstream chamber and said weight is positioned in said downstream section and wherein said upstream chamber is dimensioned to prevent said weight from entering said upstream chamber.

5. A surgically implantable drainage valve for the treatment of hydrocephalus, comprising:

a valve body having an upstream opening and a downstream opening therein and a valve chamber to establish fluid communication between said upstream and downstream openings;

valve closure means in said valve chamber to selectively open and close said upstream opening in response to changes in fluid pressure differentials across the valve, said valve closure means maintaining said upstream opening in a closed condition when said fluid pressure differential is less than a first predetermined value;

at least one weight positioned in said valve chamber and bearing against said valve closure means, said weight coacting with said valve closure means to maintain said upstream opening in a closed condition when said fluid pressure differential is less than a second predetermined value, said second predetermined value corresponding to a fluid pressure differential greater than said first predetermined value; and said valve body being implantable within the body of a living patient and said second predetermined value being in excess of variations in fluid pressure differences across the valve when the patient rises from a recumbent position.

6. The surgically implantable drainage valve of claim 5 wherein said valve body is cylindrical and said valve chamber includes upstream and downstream portions therein, said valve closure means positioned within said upstream portion and said weight positioned in said downstream portion.

7. The surgically implantable drainage valve of claim 6 wherein said upstream and said downstream portions are cylindrical with the diameter of said upstream portion being less than the diameter of said downstream portion.

8. The surgically implantable drainage valve of claim 5 wherein said valve closure means includes a tapered valve seat associated with said upstream opening and a spherical closure member configured to be seated in said valve seat, said closure member being moveable between a seated and an unseated position to close and open, respectively, said upstream opening in response to changes in the fluid pressure differential across the valve.

9. The surgically implantable drainage valve of claim 8 wherein said closure means further includes a compression spring for securing said closure member and said tapered valve seat, said compression spring having a first end and a second end, said spring positioned within said upstream portion of said valve chamber with said first end of said compression spring bearing against said closure member and said second end bearing against said weight.

10. The surgically implantable valve of claim 5 wherein said at least one weight includes first, second and third spherical members disposed within said valve chamber and downstream of said valve closure means, said first spherical member bearing against said valve closure means.

11. A surgically implantable drainage valve for the treatment of hydrocephalus, comprising:

a cylindrical valve body having an upstream opening and a downstream opening therein and a valve chamber to establish fluid communication between said upstream and downstream openings;

said cylindrical valve body dimensioned for implantation within a living patient such that said cylindrical valve body is substantially horizontal when the patient is in a recumbent position and substantially vertical when the patient is standing;

valve closure means in said valve chamber to selectively open and close said upstream opening in response to in fluid pressure differentials across the valve, said valve closure means maintaining said upstream opening in a closed condition when said fluid pressure differential is less than a first predetermined value;

at least one weight positioned in said valve chamber and bearing against said valve closure means, said weight coacting with said valve closure means to maintain said upstream opening in a closed condition when said fluid pressure differential is less than a second predetermined value, said second predetermined value corresponding to a fluid pressure differential greater than said first predetermined value; and said at least one weight and said closure means positioned within said cylindrical valve body to provide said second predetermined value when said cylindrical valve body is substantially vertically oriented.

12. The surgically implantable drainage valve of claim 11 wherein said valve chamber includes upstream and downstream portions therein, said valve closure means being positioned within said upstream portion and said weight positioned in said downstream portion.

13. The surgically implantable drainage valve of claim 12 wherein said upstream and said downstream portions are cylindrical with the diameter of said upstream portion being less than the diameter of said downstream portion.

14. The surgically implantable drainage valve of claim 11 wherein said valve closure means includes a tapered valve seat associated with said upstream opening and a spherical closure member configured to be seated in said valve seat, said closure member being moveable between a seated and an unseated position to close and open, respectively, said upstream opening in response to changes in the fluid pressure differential across the valve.

15. The surgically implantable drainage valve of claim 14 wherein said closure means further includes a compression spring for securing said closure member and said tapered valve seat, said compression spring having a first end and a second end, said spring positioned within said upstream portion of said valve chamber with said first end of said compression spring bearing against said closure member and said second end bearing against said weight.

16. The surgically implantable valve of claim 11 wherein said at least one weight includes first, second and third spherical members disposed within said valve chamber and downstream of said valve closure means, said first spherical member bearing against said valve closure means.

17. The surgically implantable valve of claim 11 wherein said at least one weight is a spherical member disposed within said valve chamber downstream of said valve closure means, said spherical member bearing against said valve closure means.

* * * * *

UNITED STATES PATENT AND TRADEMARK OFFICE
CERTIFICATE OF CORRECTION

PATENT NO.   : 5,368,556
DATED        : November 29, 1994
INVENTOR(S)  : Alain Lecuyer It is certified that error appears in the above-indentified patent and that said Letters Patent is hereby corrected as shown below:

Col. 6, line 31, "to in" should read --to changes in--.

Signed and Sealed this

Twenty-sixth Day of September, 1995

Attest:

BRUCE LEHMAN

*Attesting Officer*   *Commissioner of Patents and Trademarks*